（12） United States Patent
Strohhoefer et al.

(10) Patent No.: US 9,700,662 B2
(45) Date of Patent: Jul. 11, 2017

(54) DEVICE FOR EXTRACORPOREAL BLOOD TREATMENT

(71) Applicant: B. BRAUN AVITUM AG, Melsungen (DE)

(72) Inventors: Christof Strohhoefer, Kassel (DE); Silvie Krause, Melsungen (DE); Kai-Uwe Ritter, Rednitzhembach (DE); Joern Meibaum, Baunatal (DE)

(73) Assignee: B. BRAUN AVITUM AG, Melsungen (DE)

( * ) Notice: Subject to any disclaimer, the term of this patent is extended or adjusted under 35 U.S.C. 154(b) by 515 days.

(21) Appl. No.: 14/264,867

(22) Filed: Apr. 29, 2014

(65) Prior Publication Data

US 2014/0326646 A1 Nov. 6, 2014

(30) Foreign Application Priority Data

May 2, 2013 (DE) .................. 10 2013 104 501

(51) Int. Cl.
*B01D 61/30* (2006.01)
*B01D 61/32* (2006.01)
*A61M 1/16* (2006.01)

(52) U.S. Cl.
CPC ........ *A61M 1/1609* (2014.02); *A61M 1/1617* (2014.02); *B01D 61/30* (2013.01);
(Continued)

(58) Field of Classification Search
CPC .... A61M 1/16; A61M 1/1609; A61M 1/1617; A61M 2202/0498; A61M 2205/3306;
(Continued)

(56) References Cited

U.S. PATENT DOCUMENTS 4,083,777 A * 4/1978 Hutchisson ............. A61M 1/16
210/186
5,368,555 A 11/1994 Sussman et al.
(Continued)

FOREIGN PATENT DOCUMENTS

DE 100 38 835 2/2002
DE 101 14 283 7/2002
(Continued)

OTHER PUBLICATIONS

German Search Report with translation for DE 10 2013 104 501.4 dated Jan. 28, 2014.
(Continued)

*Primary Examiner* — Joseph Drodge
(74) *Attorney, Agent, or Firm* — RatnerPrestia

(57) ABSTRACT

A device for extracorporeal blood treatment is disclosed that includes a detection equipment for detecting uremic toxins in a used dialysis liquid by measuring the absorbance, the detection equipment being provided at such a position downstream the outflow of the dialysis liquid from a filter element that at least one of the following requirements is fulfilled: a) the filling volume of the fluid line and of the components starting from the outflow of the used dialysis liquid from the filter element to the detection equipment is less than or equal to 100 ml; and b) the length of the fluid line starting from the outflow of the used dialysis liquid from the filter element to the detection equipment is at most 250 cm.

12 Claims, 10 Drawing Sheets

(52) U.S. Cl.
CPC ..... B01D 61/32 (2013.01); *A61M 2202/0498* (2013.01); *A61M 2205/3306* (2013.01); *A61M 2205/3313* (2013.01)

(58) Field of Classification Search
CPC .. A61M 2205/3313; A61M 2205/3317; A61M 1/1605; A61M 1/1607; A61M 1/1619; B01D 61/24; B01D 61/243; B01D 61/28; B01D 61/30; B01D 61/32; B01D 2311/246; A61B 5/1455
USPC .... 210/85, 90, 93, 96.2, 321.6, 321.71, 646, 210/647, 637, 739, 741, 745; 356/39–42; 600/310; 604/6.01, 6.09, 6.1
See application file for complete search history.

(56) References Cited

U.S. PATENT DOCUMENTS

| | | | | |
|---|---|---|---|---|
| 5,403,746 | A * | 4/1995 | Bentsen | A61B 5/14539 252/408.1 |
| 6,258,027 | B1 * | 7/2001 | Sternby | A61M 1/16 210/646 |
| 6,591,126 | B2 | 7/2003 | Roeper et al. | |
| 6,861,266 | B1 * | 3/2005 | Sternby | A61M 1/16 210/645 |
| 7,077,819 | B1 | 7/2006 | Goldau et al. | |
| 8,743,353 | B2 | 6/2014 | Bado et al. | |
| 2005/0236330 | A1 | 10/2005 | Nier et al. | |
| 2006/0200064 | A1 * | 9/2006 | Gross | A61M 1/16 604/5.01 |
| 2010/0213127 | A1 * | 8/2010 | Castellarnau | A61M 1/16 210/647 |
| 2011/0144459 | A1 | 6/2011 | Akita et al. | |
| 2011/0208105 | A1 * | 8/2011 | Brandl | A61M 1/342 604/5.01 |
| 2012/0217027 | A1 * | 8/2012 | Chattaway | A62C 99/0018 169/46 |
| 2013/0105371 | A1 * | 5/2013 | Frorip | A61M 1/16 210/93 |
| 2013/0153474 | A1 * | 6/2013 | Frorip | A61M 1/16 210/93 |
| 2013/0237896 | A1 * | 9/2013 | Meibaum | A61M 1/16 604/5.04 |
| 2014/0102983 | A1 * | 4/2014 | Meibaum | A61M 1/14 210/647 |
| 2014/0190891 | A1 * | 7/2014 | Lura | A61M 1/1696 210/662 |
| 2014/0217029 | A1 * | 8/2014 | Meyer | A61M 1/3465 210/647 |
| 2014/0291534 | A1 * | 10/2014 | Ahrens | A61M 1/1694 250/373 |
| 2014/0296766 | A1 * | 10/2014 | Krause | A61M 1/1609 604/6.11 |

FOREIGN PATENT DOCUMENTS

| | | |
|---|---|---|
| DE | 10 2009 036 044 | 2/2011 |
| DE | 10 2010 032 154 | 1/2012 |
| DE | 10 2011 008 482 | 1/2012 |
| EP | 0 898 974 | 3/1999 |
| EP | 1 083 948 | 3/2001 |
| EP | 1 144 024 | 10/2001 |
| EP | 1 342 479 | 9/2003 |
| EP | 2 397 167 | 12/2011 |
| FR | 2 801 794 | 6/2001 |
| WO | WO 97/44072 | 11/1997 |
| WO | WO 99/62574 | 12/1999 |
| WO | WO 00/38761 | 7/2000 |

OTHER PUBLICATIONS

Alfred Dirksen, "Dialyse Zuhaus—Einführung in die Heim-Hämodialyse (Dialysis At Home—Introduction to home hemodialysis)," Kuratorium für Dialyse und Nierentransplantation e.V., 2007. pp. 1-92, with translation of pp. 48-49.

Translation of "Hämodialysegeräte 4008 H/S, Sichtbar bessere Dialyseergebnisse {Hemodialysis devices 4008 H and 4008 S, visibly better dialysis results)," Fresenius Medical Care, 2001 (last page).

Uhlin et al., "Haemodialysis treatment monitored on-line by ultra violet absorbance," Linköping University, Medical Dissertation No. 962, 2006.

Calia et al., "Monitoring Urea, Creatinine and B2-Microglobulin Concentrations in Spent Dialysate by Spectrophotometric and Spectrofluorimetric Measurements," 52$^{nd}$ National Congress of the Italian Society of Nephrology, Genova, Sep. 21-24, 2011.

B. J. Kirby, "Micro- and Nanoscale fluid Mechanics," Cambridge University Press, 2010. (Book).

European Search Report for EP 14165194.3 dated May 4, 2015.

* cited by examiner

DEVICE FOR EXTRACORPOREAL BLOOD TREATMENT

CROSS REFERENCE TO RELATED APPLICATIONS

This application claims priority to German application DE 10 2013 104 501.4 filed May 2, 2013, the contents of such application being incorporated by reference herein.

FIELD OF THE INVENTION

The invention relates to a device for extracorporeal blood treatment.

BACKGROUND OF THE INVENTION

Patients suffering from a restricted or lacking renal function will have the waste products of the natural metabolism (including uremic toxins) removed by renal substitution methods or dialysis methods. Here, removing the substances from the blood, which is taken from the patient and conveyed in extracorporeal manner, is performed through the contact of the blood with a dialysis liquid; in this process, the blood and the dialysis liquid are not in direct contact, but contact each other via a semi-permeable membrane. The dialysis liquid is charged with various salts. The removal of the physiological waste products is carried out through diffusive and convective effects. These are responsible for the transport of the substances from the blood to the dialysis liquid via the membrane arranged in extracorporeal manner. Having removed a part of the waste materials, the blood which has been treated in such a manner is again returned to the patient.

For evaluating the efficiency of a dialysis session, the concentrations of uremic toxins are determined before, after and possibly also during a dialysis session. The reduction of the respective substances is the central basis for the evaluation of the dialysis dosage.

Urea is a common key metabolite which is taken for determining the dialysis dosage. Correspondingly, the urea reduction rate is said to be a crucial parameter in dialysis technology. The determination of the urea reduction can be carried out in different ways.

A classic procedure is the chemical determination of the concentration of urea in the blood, each time before and after a dialysis therapy. However, the problem of this procedure is that the blood samples have to be taken from the patient and then sent to a laboratory which is provided with an appropriate equipment for determining the concentration of urea. This process may indeed take several days. Accordingly, the determination of the dialysis dosage cannot be carried out in a timely manner and especially not during a dialysis session.

DESCRIPTION OF THE RELATED ART

Another possibility of determining the dialysis dosage is to measure the UV absorption in the outflow of the dialysis liquid. Uhlin has demonstrated in his doctoral dissertation with the subject "Haemodialysis treatment monitored on-line by ultra violet absorbance", Linköping University, Medical Dissertation No. 962, 2006, that the alteration of the decadic absorption degree in the draining dialysis liquid at a wavelength of 280 nm shows a very good correlation to the change in the concentration of urea in the blood of the patient. These results have been recently confirmed by Calia et al. (Monitoring Urea, Creatinine and β2-Microglobulin Concentrations in Spent Dialysate by Spectrophotometric and Spectrofluorimetric Measurements, Calia D., Di Francesco F., Fuoco R., Ghimenti S., Kanaki A., Onor M., Tognotti D., Donadio C., 52nd National Congress of the Italian Society of Nephrology, Genova, 21 to 24 Sep. 2011).

Further, the following devices and methods are known in prior art.

US 2011/0144459 A1 describes a detector for detecting the concentration of a liquid with a blood purification apparatus in which the blood is cleaned outside the body. The detector comprises an optical emitter irradiating light into the liquid, an optical detector receiving the light of the emitter behind the liquid, and a detector which detects the intensity of the incident light.

WO 00/38761 A2 describes the determination of the distribution volume of a blood ingredient during an extracorporeal blood treatment. In this process, the concentration of a blood ingredient is changed upstream the dialyzer, the change downstream the dialyzer is measured and the distribution volume of the blood ingredient is determined from said changes.

Finally, EP 1 342 479 A1 describes a device for detecting and adjusting the flow of a dialysis solution in a hemodiafiltration process. Two pumps are distributed over the inlet branch and outlet branch of the dialysis circuit. A differential flow measuring device detects the flow differential of the dialysis solution entering the filter and leaving it. A central control unit detects output signals of the differential flow measuring device. This allows for a periodical readjustment of the control pressure of the dialysis solution in the filter and to adjust the flow of the dialysis solution and of the plasma water through the membrane of the filter.

The problems in the mentioned prior art are the high background signal noise and the shallow rise of the measuring signal for determining the concentration of physiological waste products to be removed from the blood.

SUMMARY OF THE INVENTION

Therefore, it is an object of the invention to provide a generic device for extracorporeal blood treatment, which makes it possible to achieve a better quality of the measuring signal for determining the concentration and/or determining the dialysis dosage.

The invention relates to measuring equipment for the determination of waste products in dialysis liquids during dialysis treatments, as it is described in particular in EP 1 083 948 B1 in which the structure as well as the position of the known measuring device (sensor) are explained for applications in dialysis technology. The following explanations substantially refer to a UV sensor in the dialysis, as described in document EP 1 083 948 B1. At the present day, such UV sensors are integrated in many advanced dialysis machines. Since the time when such systems have been introduced to the market, the position of said sensors has remained substantially unchanged. They are situated in the outflow of the dialysis liquid, usually arranged behind the balancing equipment, i.e. downstream of the balancing equipment. The length of the lines/tubes carrying the dialysis liquid between the dialyzer and the measuring equipment normally amounts to more than 450 cm at this position, and the entire volume of the dialysis liquid between the dialyzer and the measuring equipment is approximately 200 ml. In addition, further sensor systems are known, as they are described by way of example in DE 10 2011 008 482 A1 or EP 2 397 167 A1. The document DE 10 2011 008 482 A1 describes a UV detector arrangement comprising a measuring cuvette including a wall which is transparent to UV at least in sections, with two UV LEDs with different emission wavelengths, a broadband UV detector or two narrow-band UV detectors (each of them for one of the emission wavelengths) being arranged on the measuring cuvette. EP 2 397 167 A1 describes a measuring equipment for determining the luminescence of the used dialysis liquid. The following explanations similarly apply to all sensor systems which deliver a measure for the concentration of uremic toxins in the used dialysis liquid.

Apart from the previous use for the (quasi) static determination of a measure for the concentration of uremic toxins, the quantification of transients, i.e. temporal courses of concentration changes, becomes more and more predominant. Concentration transients deliver information about dynamic patient and machine parameters wtube knowledge allows a physician to improve the quality of the therapy individually for each patient. The current positioning of the UV measuring equipment exhibiting a long fluid-carrying path and/or a high volume between the dialyzer and the measuring equipment, however, brings about some unfavorable effects. On the one hand, the draining dialysis liquid flows through a series of fluid-carrying elements on its way between the dialyzer and the UV measuring device, which due to their volume contribute to the fact that concentration changes are leveled out and cannot be temporally resolved any more. Convective mixing effects occur here which will change the transients to a large extent, right up to a complete dispersal of their information content. In the resultant measuring signal, it is frequently not possible to distinguish with certainty if there is a case of a temporarily occurring concentration peak of the waste product in question or a longer-lasting increase. The information about patient and therapy which are comprised in the transients, will get lost here. Typical elements in the dialysis liquid drain of a dialysis machine which bring about this effect are balancing equipments, e.g. balance chambers or air separators.

On the other hand, there will be a significant temporal delay between the occurrence of a concentration or concentration change in the dialysis liquid of the dialysis liquid-side chamber of the dialyzer and its proof by means of the measuring device. It may happen that several minutes lapse until the arrival of the signal at the measuring equipment. This period in time during which the used dialysis liquid is transported from the dialyzer to the measuring equipment, has the effect that transients will change also by the diffusion of uremic toxins because of the concentration gradients naturally existing there. Here again, there will be a loss of information.

Whereas the degeneration of the transients due to convectively acting elements can be prevented by arranging the measuring equipment between the dialyzer and the respective elements, the avoidance of any diffusive degeneration of the transient signal requires further considerations:

As a typical representative for small-molecular uremic toxins, urea has a diffusion coefficient in an aqueous environment of $D=1.38*10^{-5}$ cm$^2$/s, and potassium as a typical electrolyte which is present in the blood and dialysis liquid possesses a larger diffusion coefficient of $D=2*10^{-5}$ cm$^2$/s. As the Reynolds number is dimensioned in the tube of the dialysis liquid outflow such that there are laminar flow conditions, the degeneration of a sharp transient, which comes into existence e.g. due to a valve switching operation, can be estimated by means of the following relation between the diffusion time and the diffusion distance, which is derived from Fick's laws:

$$x = 2\sqrt{Dt}$$

Herein, D represents the diffusion coefficient of the substance in question in the relevant carrier medium (here: the dialysis liquid), t is the time during which the diffusion proceeds and a diffusion profile develops, and x is a measure for the width of the developing diffusion profile.

The application of this estimation to the above-mentioned substances results in typical diffusion distances from 300 to 350 μm for a diffusion time of 1 min. Having typical dialysis liquid flows and tube diameters, this results in a fringing in the signal on the scale of some milliseconds, which is already in the range of the switching periods of quick valves and has a corresponding relevance e.g. in the discrimination of artifacts from switching operations for control processes.

The above evaluation of the diffusion effect has been carried out under the assumption of a constant flow distribution over the cross-section of the dialysis liquid channel or tube (so-called top hat profile). This assumption has been made to be able to isolate the effects of the diffusion. In actual laminar flow systems, there is instead a parabolic profile (B. J. Kirby, Micro- and Nanoscale fluid Mechanics, Cambridge University Press, 2010) in the following form:

$$u_z = -\frac{1}{4\eta}\frac{\partial \rho}{\partial z}(R^2 - r^2)$$

Herein, $u_z$ is the speed of the liquid along the channel or tube, η is the viscosity of the liquid, $$\frac{\partial \rho}{\partial z}$$

is the pressure gradient, R is the inner diameter of the channel or tube, and r is the radial distance of the observed point from the center of the channel or tube. The maximum flow speed $$u_z^{max} = -\frac{1}{4\eta}\frac{\partial \rho}{\partial z}R^2$$

will appear in the center of the channel or tube for r=0. At the periphery of the channel or tube, $u_z$=0. As a function of the maximum flow speed, the parabolic flow profile can be written in simplified form as $$\frac{u_z}{u_z^{max}} = 1 - \left(\frac{r}{R}\right)^2$$

This parabolic flow profile has the effect that any concentration changes which occur at a place z=0, can be measured with sufficient precision at a place z>0 only after a finite time t. This time t is longer than the time $$t_0 = \frac{R^2\pi}{Q}z$$

which would arise if the liquid had the same speed over the entire cross-section of the channel or tube. Herein, Q is the volume flow of the medium in the channel or tube. This effect which is due to the flow profile impairs the quality of measurements which have to be performed within a specific time after the emergence of the impulse. This may be the case, for example, if a control algorithm requires a data value in short time intervals or if only a short concentration impulse is available for the measurement.

In order to understand this, the following deliberations are made:

The median flow speed in the channel or tube can be determined from the volume flow of the liquid Q and the geometry:

$$\bar{u} = \frac{Q}{R^2 \pi}$$

In addition, the median speed as a function of the maximum speed can be determined from the parabolic flow profile:

$$\bar{u}_z = \frac{\int_0^R u_z(r) \cdot r\, dr}{\int_0^R r\, dr} = \frac{u_z^{max}}{2}$$

With this, the speed profile can be written as a function of the volume flow instead of the maximum speed:

$$u_z(r) = 2\frac{Q}{\pi R^2}\left[1 - \left(\frac{r}{R}\right)^2\right]$$

Now, it is possible to define two zones at a place z>0: a zone in the center with $0<r<r'$, where a high flow speed prevails and to which liquid with the new concentration (c, here in the following according to definition the higher concentration) has already been transported, and a second zone at the periphery $r'<r<R$, where there is still some liquid with the old concentration ($c_0$ in the following, according to definition concentration 0). The limit between these zones at r' can be determined via $$u_z(r') = 2\frac{Q}{\pi R^2}\left[1 - \left(\frac{r'}{R}\right)^2\right] = \frac{z}{t}$$

Solved to $r'^2$ results in $$r'^2 = 1 - \frac{1}{2}\frac{\pi R^2}{Q}\frac{z}{t}$$

The median concentration $\bar{c}$ in the point z>0 at time t>0 will appear as a weighted average from c and $c_0$:

$$\bar{c} = r'^2 \pi \cdot c + (R^2 - r'^2)\pi \cdot c_0$$

FIG. 6 shows the course of the median concentration versus time for measuring sites with different distances to the point of origin of a concentration jump or concentration change. The concentration jumps from $c_0=0$ to $c=1$ at time $t=0$ at place $z=0$. By way of example, the assumptive tube diameter is 0.6 cm, the assumptive volume flow is 300 ml/min. The illustration shows clearly that the laminar parabolic flow profile has the effect that—already at a distance of few decimeters—the concentration information is available only after several seconds even with the appraisal of a moderate precision of 5%.

This will become problematic especially if the concentration change to be determined exists only for a limited period of a few seconds (e.g. as described in EP 1 083 948 B1) or if information is to be obtained from the transient of the signal.

This will become clear from FIG. 7 showing the temporal course of the concentration for different positions of the measuring device with distances z>0 for a volume flow of 100 ml/min and an impulse length of 100 cm (concentration c=1). The fading of the edges of the impulse can be seen very clearly. Moreover, the concentration c will not be reached any more already with distances of smaller than 10 cm.

The theoretical observations according to FIG. 7 are confirmed by an experimental measurement of the UV absorbance, as illustrated in FIG. 8. Here, at time t=10 sec a bolus of a urea solution of 40 mg/l was injected into a dialysis tube system with a dialysis liquid flow of 300 ml/min directly upstream of a sensor 1. Urea is a uremic toxin which is removed during the dialysis. The selected concentration corresponds to a typical concentration in the dialysis liquid during a dialysis. The administration of the bolus lasted for 11 sec. The sensor 1 detects the bolus as a sharp peak in the decadic absorption measure which is directly proportional to the concentration. The diagram shows a well defined bolus with sharp edges. The value of the decadic absorption measure at the plateau of approximately 1.7 corresponds to the absorption of the urea. Downstream of the sensor 1, the dialysis liquid (and the concentration bolus injected therein) have moved through a tube segment with a length of 220 cm, at the end of which a second UV sensor was attached. The decadic absorption measure as measured by the sensor 2 is likewise shown in FIG. 8. The following can be clearly seen:

(a) A delay of the leading edge of the bolus by 5 sec, which is due to the route length between the sensors. A further result is that (b) the decadic absorption measure reaches its plateau only 8 sec after the start of the bolus, compared to 1 sec for sensor 1. In quantitative terms, it can be stated that (c) at sensor 2, the plateau of the decadic absorption measure is 20% lower than that for sensor 1—this results in a corresponding error in the determination of the concentration. Finally, (d) a falling edge can be identified in the signal of sensor 2 with a length of 7 sec, compared to the edge with a length of 1 sec of the same bolus in sensor 1.

Hence, FIG. 8 shows clearly that the signal quality deteriorates in the experiment with respect to the achievement of the plateau and the definition of the edges of a bolus; the longer the distance between the sensor and the point of origin of the bolus, the more pronounced is said deterioration.

It will be apparent from FIGS. 6, 7 and 8 that the rise (the sharpness) of the edges and the (prompt) achievement of c depend to a high degree on the position of the measuring device. The quality of the leading edge as well as the error in the determination of the concentration become smaller, the shorter the distance is between the measuring device and the point of origin of the concentration change (concentration jump).

The precision of the determination of the concentration shall serve as an example, resulting at time t=0.1 min from FIG. 6. Having a distance of 10 cm between the measuring device and the point of origin of the concentration change, the concentration c will be determined under the mentioned prerequisites with an error of less than 0.05%. Compared to this, the error for a distance of 200 cm already amounts to 8.5%. The latter error is already unusable for a precise control of therapy parameters.

FIG. 5 shows a further experimental support of the considerations illustrated above. Here, a sharp concentration impulse of a substance of 300 ml was injected into the dialyzer exhibiting a dialysis liquid flow of 500 ml/min. The diagram shows the response of a UV measuring device which was attached approximately 100 cm behind the outflow of the dialyzer. The experiment was repeated several times and shows similar results each time, corresponding to the illustration in FIG. 7, in fact the edge which rises already before the nominal arrival of the concentration impulse, the sustained falling edge, as well as a maximum concentration beneath $c_0$. It goes without saying that the experimental results include, apart from the influence of the parabolic profile on the measuring accuracy, also effects of the diffusion as well as any additional convective effects due to enlargements/reductions of the cross-section in the channel or tube which in their entirety increase the effects which are detrimental to the measurement.

In the dialysis, the point of origin of a concentration change or of a concentration impulse is the dialyzer in most cases. Accordingly, a solution to the described problem is, according to aspects of the invention, to fulfill the condition that the measuring device is spaced from the outflow of the used dialysis liquid from the dialyzer at most 250 cm, preferably less than 200 cm, preferably less than 150 cm, preferably less than 100 cm, preferably less than 50 cm, preferably less than 20 cm tube or channel length.

Above calculations have been carried out under the assumption of constant diameters of channels and/or tubes. However, this is not necessarily the case in dialysis machines. Due to variations in the channel or tube diameter, caused e.g. by coupling pieces, valves and other fluidic elements, and the concomitant changes in the flow speed at a constant volume flow, the above approach can be transferred in analogy to volumes between the point of origin of a concentration change and the position of the measuring device as a second, additional or alternative condition. According to said second condition, an advantageous positioning of the sensor should be according to aspects of the invention less than or equal to 150 ml (filling volume of lines and components) as from the outflow of the used dialysis liquid from the dialyzer to the sensor, preferably less than or equal to 100 ml, preferably less than or equal to 50 ml, preferably less than or equal to 35 ml, preferably less than or equal to 20 ml for a (median) channel/tube cross-section of preferably approximately 3 to 7 mm (further preferred approximately 5 mm) and in consideration of the dialysis liquid volume of the components provided in the dialysis liquid path.

It has been found on the basis of the above theoretical and analytical considerations that arranging the detection/measuring device (sensor) at the proximal portion (i.e. the portion close to the dialyzer) of the outflow of the dialysis liquid from the dialysis liquid-side chamber of a filter element solves the given problem and overcomes the problems of the prior art which have been described above if at least one of the two requirements is fulfilled.

The device, according to aspects of the invention, for extracorporeal blood treatment has, among others, preferably the following components:

a filter element (dialyzer) which is subdivided into a blood-sided chamber and a dialysis liquid-side chamber and comprises an inflow for a fresh dialysis liquid to the dialysis liquid-side chamber and an outflow for the used dialysis liquid from the dialysis liquid-side chamber, a balancing equipment provided downstream of the filter element, a detection/measuring equipment (sensor) adapted to detect the concentration of at least one metabolic product from the blood of the patient on the dialyzer liquid side in continuous or clocked fashion, a housing whose inside accommodates, among other things, at least the balancing equipment and preferably the detection/measuring device, and outside of which the filter element is arranged, as well as a fluid line feedthrough through the housing, via which the filter element is connected or can be connected to the balancing equipment in fluidic terms, wherein the detection/measuring device is arranged on the fluid line feedthrough (directly downstream of it) preferably internally in the housing.

In this arrangement, the device, according to aspects of the invention, for extracorporeal blood treatment may additionally comprise further components which are known from the prior art per se and belong or will belong to the standard equipment of advanced dialysis machines, such as a pressure measuring device preferably in/on the housing wall in the vicinity of the fluid line feedthrough and hence immediately upstream the detection/measuring device and/or a bypass line which bypasses the filter element and is disposed preferably downstream of the detection/measuring device or alternatively upstream of the detection/measuring device, in that case inter alia for the purpose of calibrating the detection/measuring device. As these further components are only of secondary importance for the present invention, however, they are not set forth in detail for the sake of clarity.

The device, according to aspects of the invention, for extracorporeal blood treatment may include any apparatus which are suitable for dialysis, in particular artificial kidneys and dialysis machines. The invention offers the advantage of improving the measuring accuracy and sharpness of the measuring signal for determining the concentration of physiological waste products to be removed from the blood. Thus, the problems involved in an extracorporeal blood treatment which have been depicted above are solved and the identification and quantification of concentration changes are made possible with particularly accuracy.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

The Figures are purely illustratively and therefore not true to scale. Identical elements or elements having the same effect are provided with identical reference symbols, unless otherwise stated.

Figure 1:
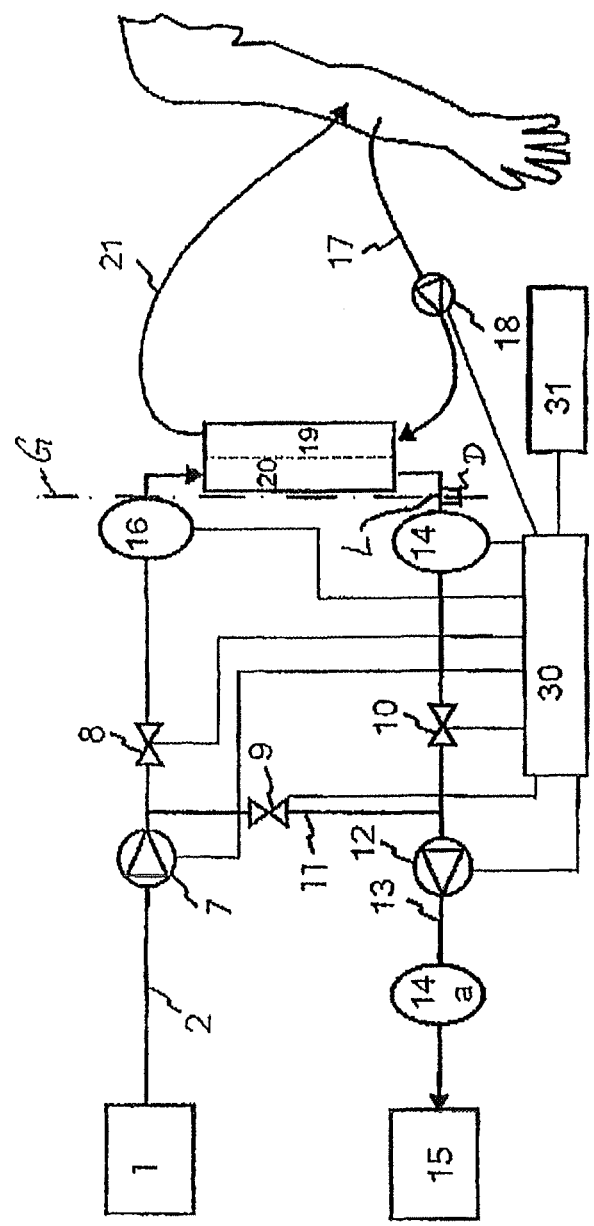
FIG. 1 shows a dialysis liquid circuit comprising a device for extracorporeal blood treatment intended for hemodialysis.

FIG. 1 shows a first embodiment of the dialysis liquid circuit according to aspects of the invention in a device for extracorporeal blood treatment (e.g. a dialysis machine). Here, the device is used for carrying out a hemodialysis without any substitution of liquid. Fresh dialysis liquid is supplied from a dialysis liquid source 1 and fed into the circuit via an inflow 2. To this end, a flow pump (FPE) 7 is provided upstream of a filter element (dialyzer). A first valve (VDE) 8 between the flow pump 7 and the filter element closes or opens an inlet of the filter element. A second valve (VDA) 10 downstream of the filter element opens or closes the dialysis liquid circuit with respect to an outlet of the filter element. In analogy to the inlet side, the outlet side of the filter element is also provided with a flow pump 12 which transports the used dialysis liquid to the dialysis liquid outlet from where it is discharged/disposed via a dialysis liquid outflow line 13 to a dialysis liquid outflow 15. The input-side flow pump 7 and the output-side flow pump 12 are connected to each other via a bypass line 11 which is connected to the dialysis liquid circuit in such a manner that it selectively bypasses the filter element. To this end, the bypass line 11 can be closed and opened by a bypass valve (VBP) 9 and is arranged upstream of the first valve 8 and downstream of the second valve 10.

According to aspects of the invention, a detection/measuring device 14 is provided close to the filter element (dialyzer), i.e. between the outlet of the filter element and the bypass line 11, preferably between the filter element outlet and the second valve 10. In addition or as an alternative, a detection/measuring device 14a is arranged downstream of the bypass line 11.

At this point, reference is made to the fact that in the present device for extracorporeal blood treatment, the filter element is situated outside a housing G illustrated in FIG. 1 by a dot-and-dash line, whereas the detection equipment 14, 14a is enclosed in the housing G. Optionally, a pressure sensor D is arranged in or on the housing wall preferably upstream of the detection equipment 14, 14a. It is further preferred that the detection equipment 14 is arranged directly on the housing wall, i.e. immediately on a line feedthrough L which establishes a fluid connection between the housing-external line section starting from the filter element outlet and the housing-internal line section. In this way, the detection equipment 14 within the housing is protected and nevertheless arranged as close as possible to the filter element in terms of line/flow technology.

Usually, lines (tubes) are used which have a line inner cross-section of approximately 3 to 7 mm, preferably 5 mm. According to aspects of the invention, the length of the line between the filter element outlet and the detection equipment 14 or 14a amounts to at most 250 cm, preferably less than 200 cm, preferably less than 150 cm, preferably less than 100 cm, preferably less than 50 cm and more preferably less than 20 cm length of the tube or channel. Alternatively or in addition to this, an advantageous positioning of the detection equipment 14 or 14a (i.e. of the sensor) exists if the volume of the tubes and lines between the filter element outlet and the detection equipment 14 or 14a is less than or equal to 100 ml, preferably less than or equal to 50 ml, preferably less than or equal to 35 ml, preferably less than or equal to 30 ml, preferably less than or equal to 15 ml and more preferably less than or equal to 7 ml, also in each case preferably with a flow cross-section of approximately 3 to 7 mm (approximately 5 mm). Here, reference is made to the fact that—depending on the model of the dialysis machine and with a tube length of less than 100 cm or with a volume of less than 20-30 ml—the sensor will be positioned outside the machine housing, so that enclosing the sensor in the housing is worthwhile but not always realizable in principle.

By means of a flow measuring device 16 between the first valve 8 and the filter element, the fluid volume flow circulated in the circuit is optionally determined/measured.

The patient can be connected to the device for extracorporeal blood treatment (dialysis machine) via an arterial tube system 17. An arterial blood pump (BPA) 18 is provided or adapted to remove uncleaned blood from the patient and to supply it to a blood side (BS) 19 in the filter element; said blood side is in connection with a dialysis liquid side (DS) 20 in the filter element via a semi-permeable membrane. From the blood side (BS) 19 in the filter element, cleaned blood can be returned to the patient via a venous tube system 21.

An arithmetic unit 30 comprising a user interface 31 controls the circuit and the components for the circulation of the fluid on the dialysis liquid side as well as on the blood side.

Figure 2:
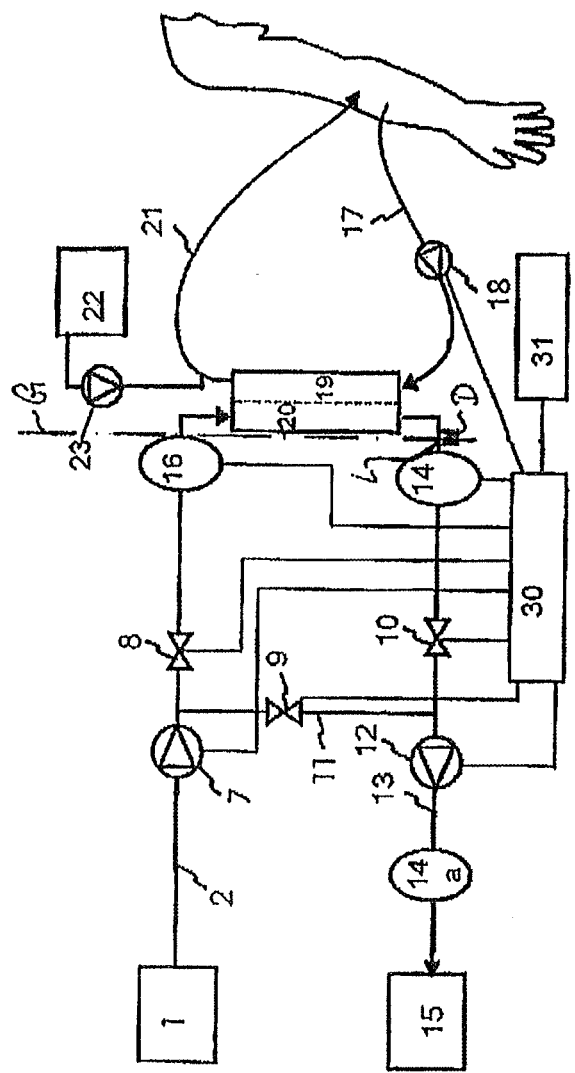
FIG. 2 shows a dialysis liquid circuit comprising a device for extracorporeal blood treatment intended for hemodiafiltration.

FIG. 2 shows a further embodiment of the dialysis liquid circuit according to aspects of the invention in a device for extracorporeal blood treatment. As in the embodiment according to FIG. 1, the detection equipment 14, 14a can be positioned alternatively or in combination at two different places in the outflow of the used dialysis liquid, namely close to the filter element (dialyzer) at position 14 between the dialyzer and the bypass 11 or second valve 10, preferably directly (preferably without an intermediate line) on (the inside or outside) of the line feedthrough L through the housing G, or additionally or alternatively behind the bypass line 11 (or flow pump 12) at position 14a if in the latter case the above-mentioned requirements regarding the maximum line length and/or line volume are fulfilled. In contrast to the embodiment according to FIG. 1, however, FIG. 2 shows a device for carrying out a hemodiafiltration with substitution. The substitution liquid is infused here on the blood side downstream of the dialyzer by a substitution pump 23 from a substitution liquid reservoir 22 into the blood circulation. This results in a convective purification of the blood. There exists the possibility (not illustrated, but realizable in a similar way) to infuse the substitution liquid at the blood side upstream of the dialyzer into the blood circulation or to infuse it upstream as well as downstream of the dialyzer.

Figure 3:
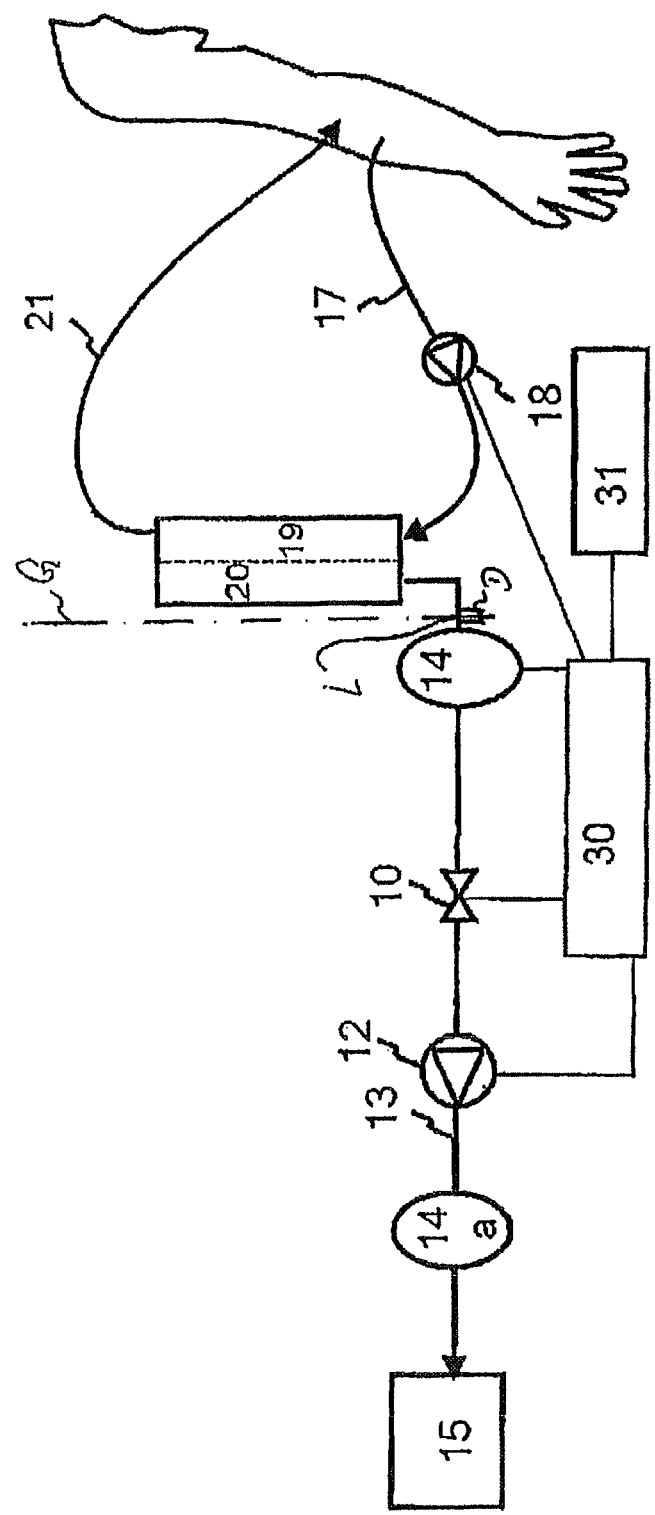
FIG. 3 shows a dialysis liquid circuit comprising a device for extracorporeal blood treatment for the extraction of liquid during a sequential therapy.

FIG. 3 shows the blood treatment device (dialysis machine) for carrying out a sequential phase (pure ultrafiltration) without any substitution of liquid. According to this, in particular a further dialysis liquid circuit is shown, in which the detection equipment 14, 14a is arranged (or may be arranged) alternatively or in combination at two different places in the outflow of the used dialysis liquid. According to aspects of the invention, the detection equipment is close to the dialyzer (immediately internally or externally on the line feedthrough L leading into the housing interior) at position 14 between the dialyzer and the second valve 10, and additionally or alternatively the detection equipment is arranged downstream of the valve 10 at position 14a (if the requirement regarding the line length and/or volume is fulfilled).

Figure 4:
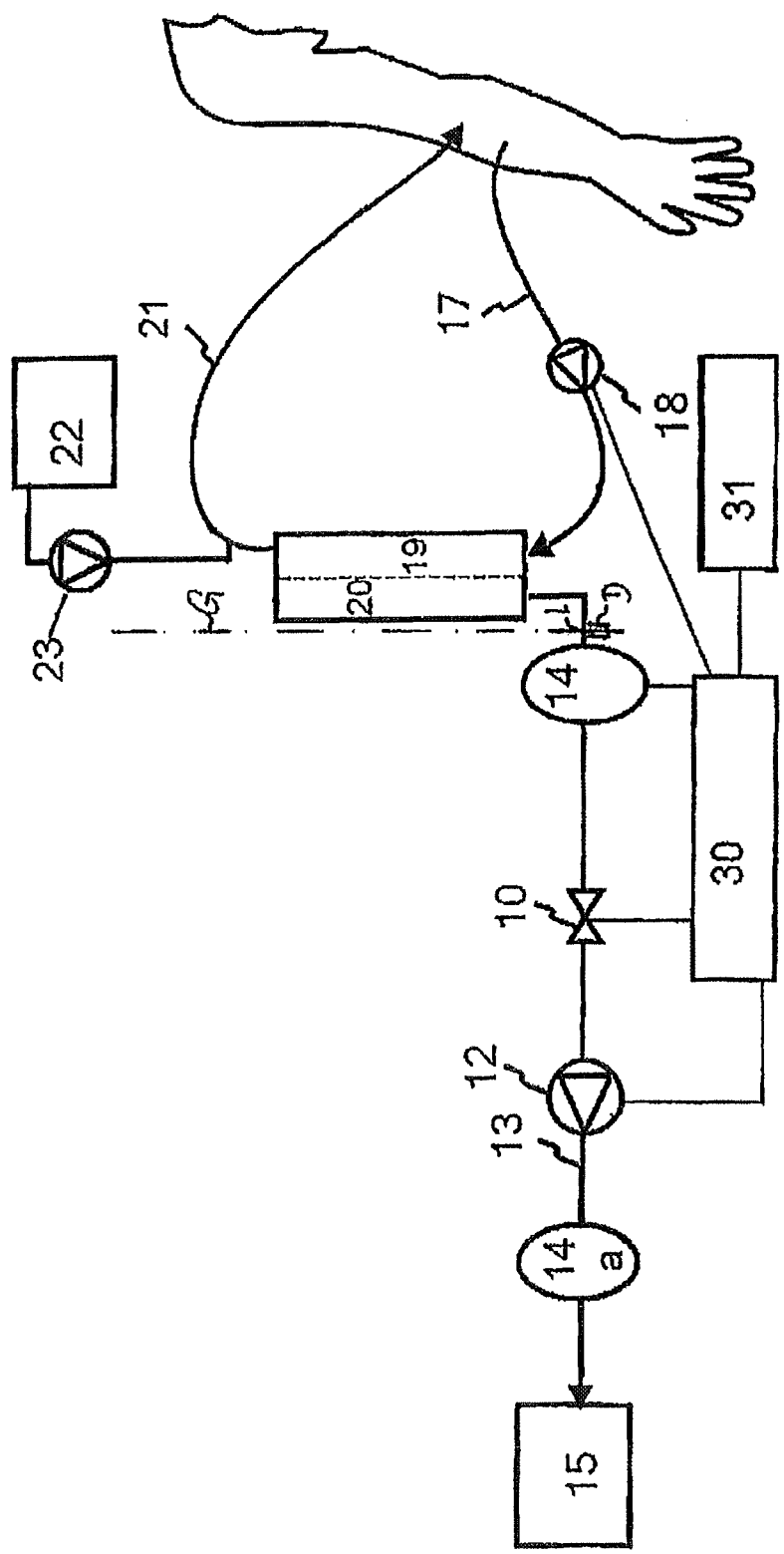
FIG. 4 shows a dialysis liquid circuit comprising a device for extracorporeal blood treatment intended for hemofiltration.

FIG. 4 shows yet another dialysis liquid circuit in a device for extracorporeal blood treatment, which in the present case is used for a hemofiltration, according to which the detection equipment 14, 14a is disposed alternatively or in combination at two different places in the outflow of the used dialysis liquid, according to aspects of the invention close to the dialyzer (directly on/after the line feedthrough L leading through the housing G) at position 14, and in addition or alternatively downstream of the valve 10 at position 14a (in compliance with the above-mentioned requirement with respect to the line length and/or line filling volume). Here, the substitution liquid is infused into the blood circulation by means of a substitution pump 23 from a substitution liquid reservoir 22 at the blood side downstream and/or upstream of the dialyzer.

Figure 5:
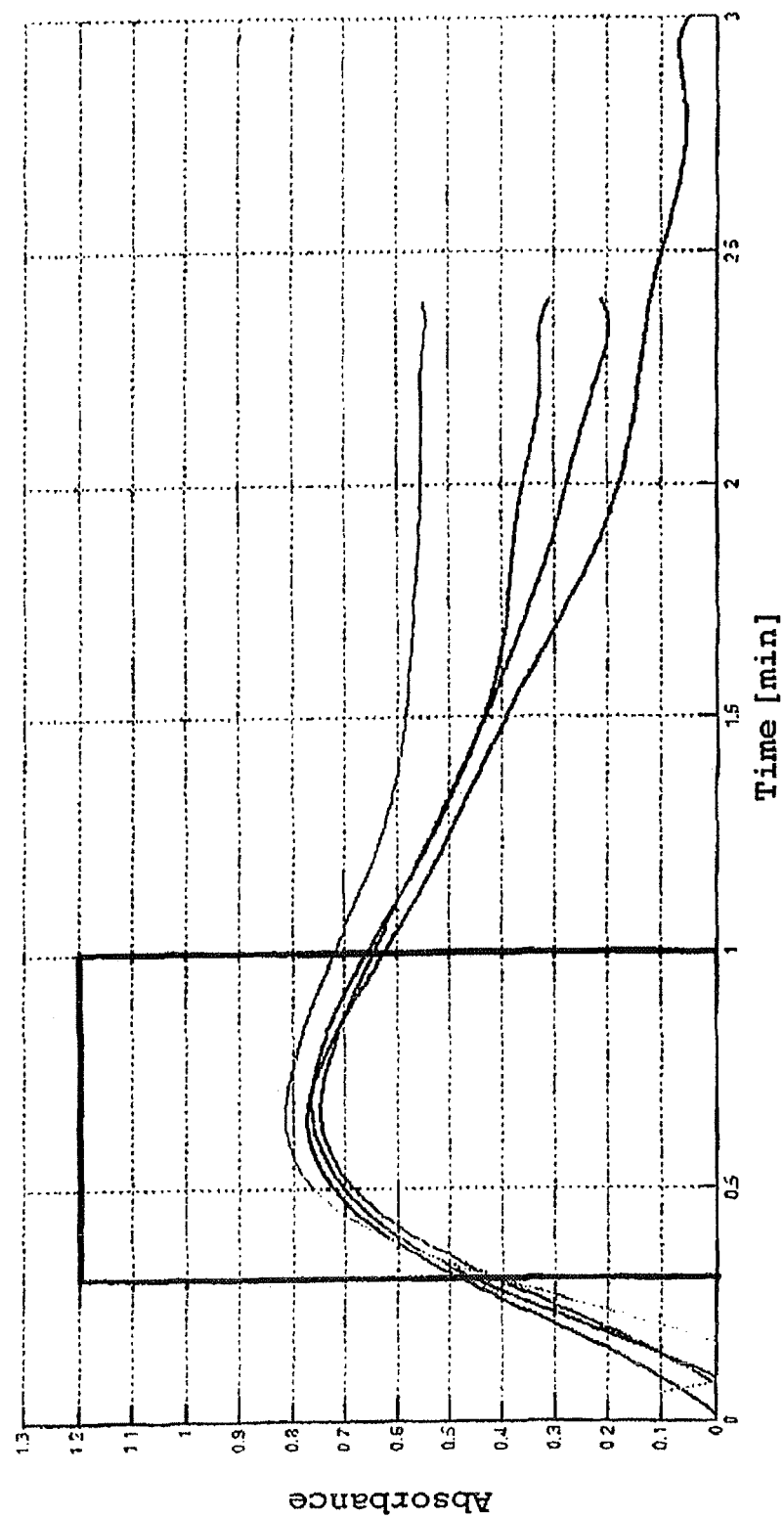
FIG. 5 shows, as already described, the response of a UV measuring device at a place according to the prior art.
Figure 6:
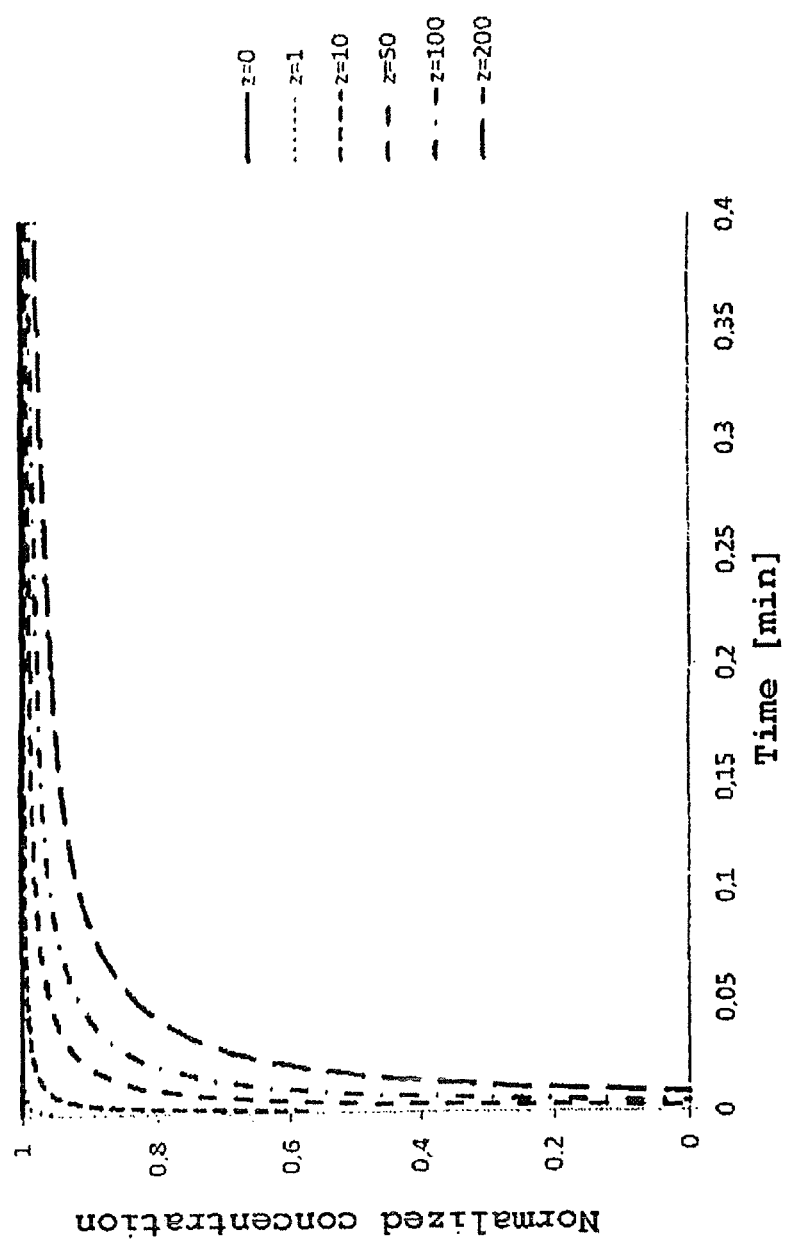
FIG. 6 shows, as already described, the course of the concentration versus time for different positions of the measuring device after an abrupt concentration change.
Figure 7:
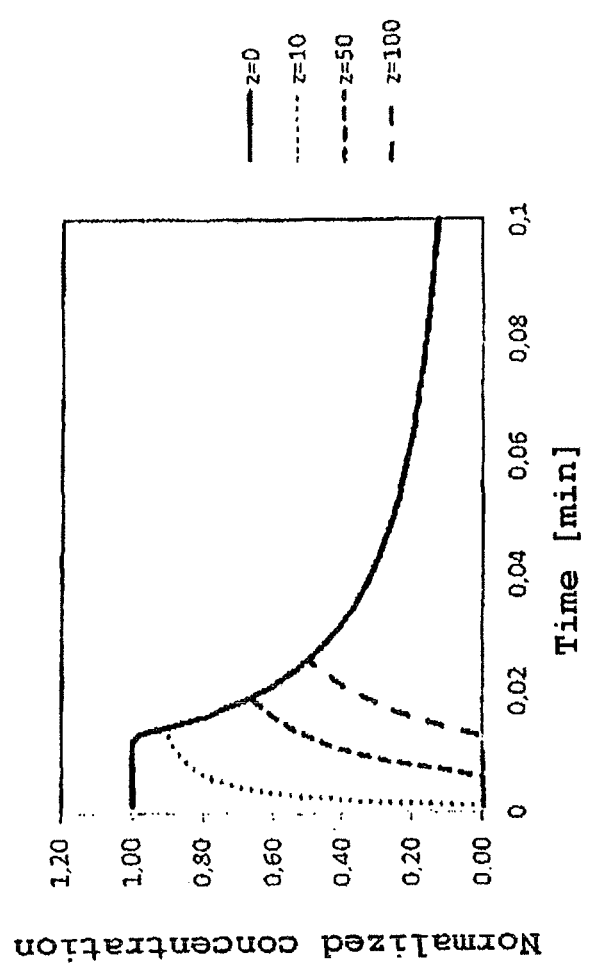
FIG. 7 shows, as already described, the response of a UV measuring device to a concentration impulse with the device according to aspects of the invention, as a function of its positioning.
Figure 8:
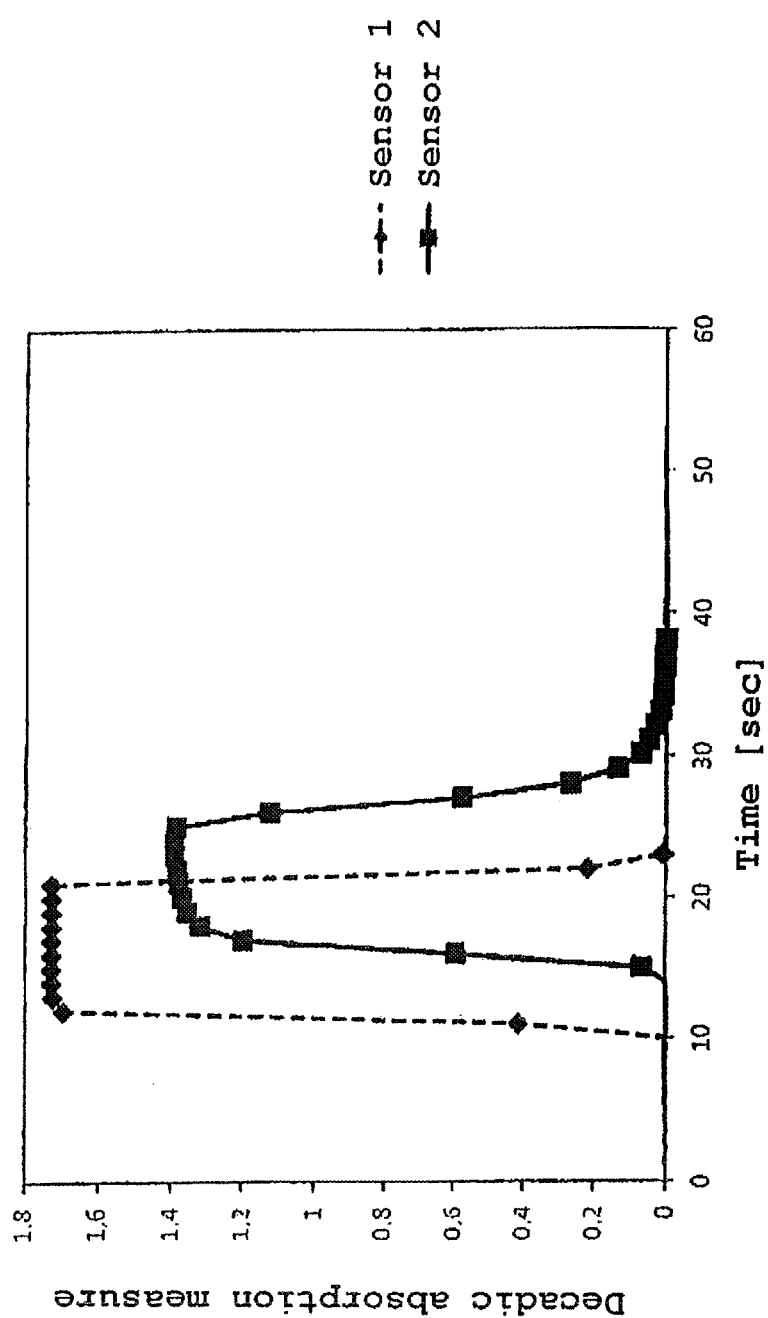
FIG. 8 shows, as already described, the UV absorbance after a bolus, as it is detected by a first sensor and a second sensor.

FIG. 5 shows the response of the detection equipment (in the present case in the form of a UV measuring device) to a concentration impulse at the filter element, here a dialyzer, if the UV measuring device is arranged according to the prior art. There are shown four measurements under identical conditions, demonstrating the variance of the system response caused by the fluid path of more than 450 cm. The Figure shows the response of the UV sensor to a concentration impulse which should be perceived as a rectangular impulse (as shown in the illustration) in the absence of the diffusion and convection effects which are caused by the guidance of the fluid. The diffusion effects as well as the flow profile in the lines/tubes also have the effect that the concentration sensed by the UV sensor begins to rise already before the normal delay time.

Figure 10:
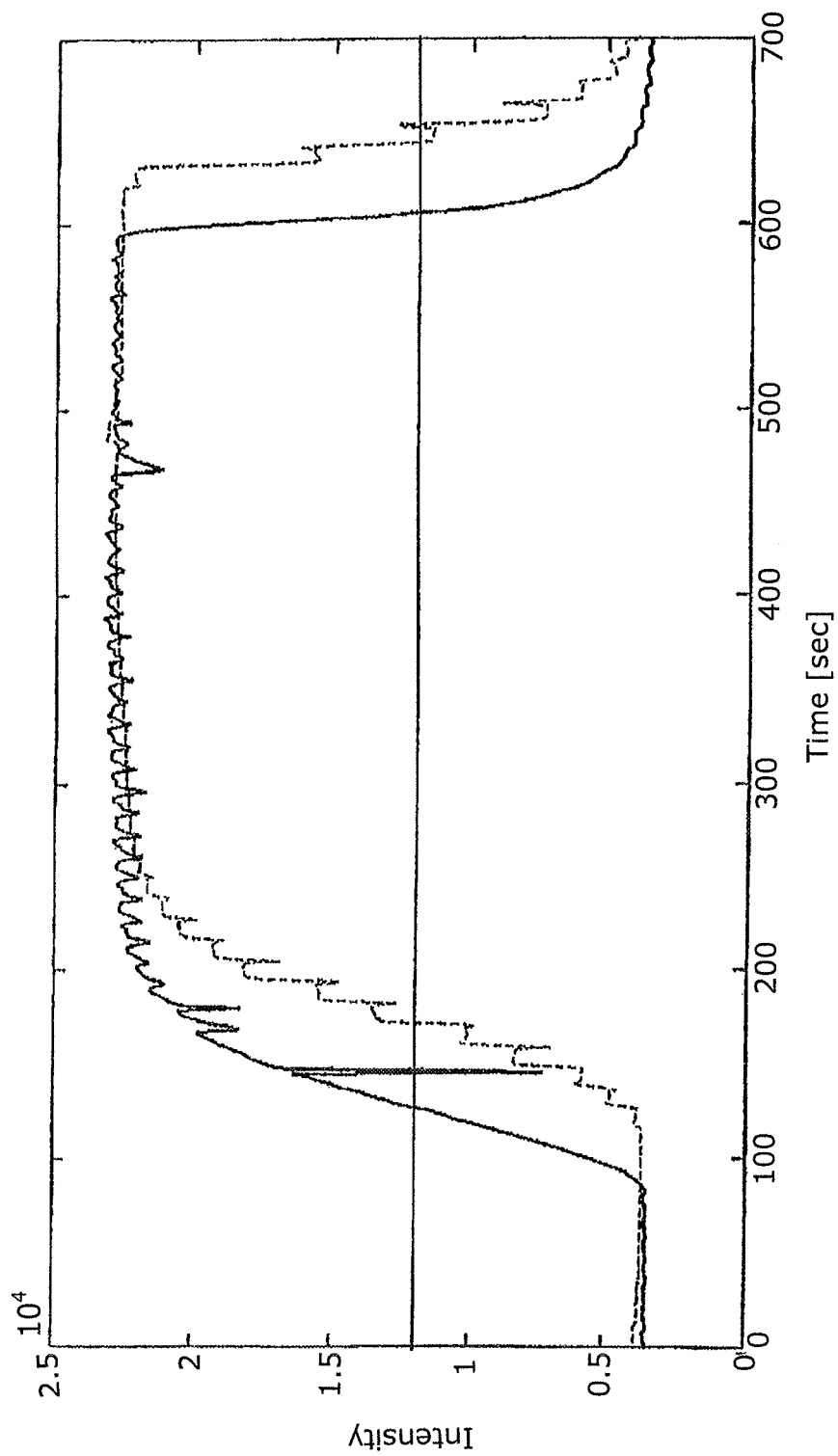

In contrast to this, FIG. 10 shows the response of a UV measuring device to a concentration impulse if the UV measuring device is provided at such a place in the dialysis liquid-side area in the outflow line downstream of the filter element, which does not fulfill the above requirements with respect to the line length and/or line filling volume (dashed line), and the response if the UV measuring device is provided at such a place in the dialysis liquid-side area in the outflow line downstream of the filter element, which fulfills the above requirements regarding the line length and/or line filling volume (solid line). The measurement at the place which does not fulfill the requirements (for instance behind the balancing equipment) shows a delay of approximately 30 sec compared to the measurement at the place fulfilling the requirements. In addition, the measurement at the place (which does not fulfill the requirements) downstream of the balancing equipment according to FIG. 10 shows steps in its increase, which are dictated in this case by the way of operation of the upstream balancing equipment (mechanical switching process). They reduce the signal quality of the increase and make its evaluation more difficult.

Optional Configurations of the Invention

The invention is not limited to the embodiments described above. In terms of the present invention, the place fulfilling the requirements is to be understood by design as that area of the outflow of the dialysis liquid from the dialysis liquid-side chamber of the filter element which immediately adjoins the outflow nozzle of the dialysis liquid-side chamber of the filter element but preferably is still within the device housing.

Consequently, said line section may extend—depending on the dimensioning of the blood treatment device as well as the location of the filter element—at the utmost from the outflow nozzle of the dialysis liquid-side chamber of the filter element to the inlet into the balancing equipment. The portion may further comprise a rinsing bridge. Having such a structure, the detection equipment may be situated upstream or downstream of the rinsing bridge; according to aspects of the invention, however, it is arranged in any case upstream of the balancing equipment, to prevent a falsification and deterioration of the signal, caused by the balancing equipment. Whereas the detection equipment is arranged preferably within the device housing, so as to protect it against external forces, it may also be attached externally (i.e. outside the housing) on the device for extracorporeal blood treatment, in particular if this is the only way to be able to fulfill the above-mentioned requirements with respect to the line length and/or line filling volume. The term "as far as to the detection equipment" further designates the place where the measurement is carried out in or on the detection equipment. Preferably, this is the place where e.g. in the case of a UV sensor the optical measuring beam travels through the dialysis liquid.

It is preferred that the line section between the filter element and the detection equipment comprises according to the above definition not more than the area from the outflow of the filter element up to the balancing equipment. Preferred is an area of 250 cm (line length) in the direction of flow from the outlet or outflow of the filter element toward the balancing equipment, further preferred 200 cm, still further preferred 150 cm, still further preferred 100 cm, still further preferred 90 cm, still further preferred 80 cm, still further preferred 70 cm, still further preferred 60 cm, still further preferred 50 cm, still further preferred 40 cm, still further preferred 30 cm, still further preferred 20 cm and most preferred is a length of 10 cm from the outlet or outflow of the filter element toward the balancing equipment.

It is further preferred that this application relates to a device for extracorporeal blood treatment, in which the detection equipment is a UV measuring device. The latter comprises at least one radiation source and at least one sensor. Candidates for radiation sources are UV LEDs, UV lasers and broadband radiation sources such as deuterium lamps. The sensors are selected from the group consisting of photo diodes, photo transistors, CCD and CMOS detectors, photomultipliers or photon-counting modules or elements of comparable function. It is likewise preferred if the sensor of the UV measuring device operates at least in the wavelength range from 200 to 350 nm. This wavelength range is of particular interest, as many metabolites and physiological waste products which are important for excretion have a characteristic absorption peak in this wavelength range, for instance urea at 290 nm, creatinine at approximately 235 nm, hippuric acid at approximately 260 nm and creatine at approximately 210 nm. Such a characteristic absorption peak or a combinatorial analysis of a plurality of such peaks offers the opportunity to draw conclusions on the respective concentration of the metabolite.

Figure 9:
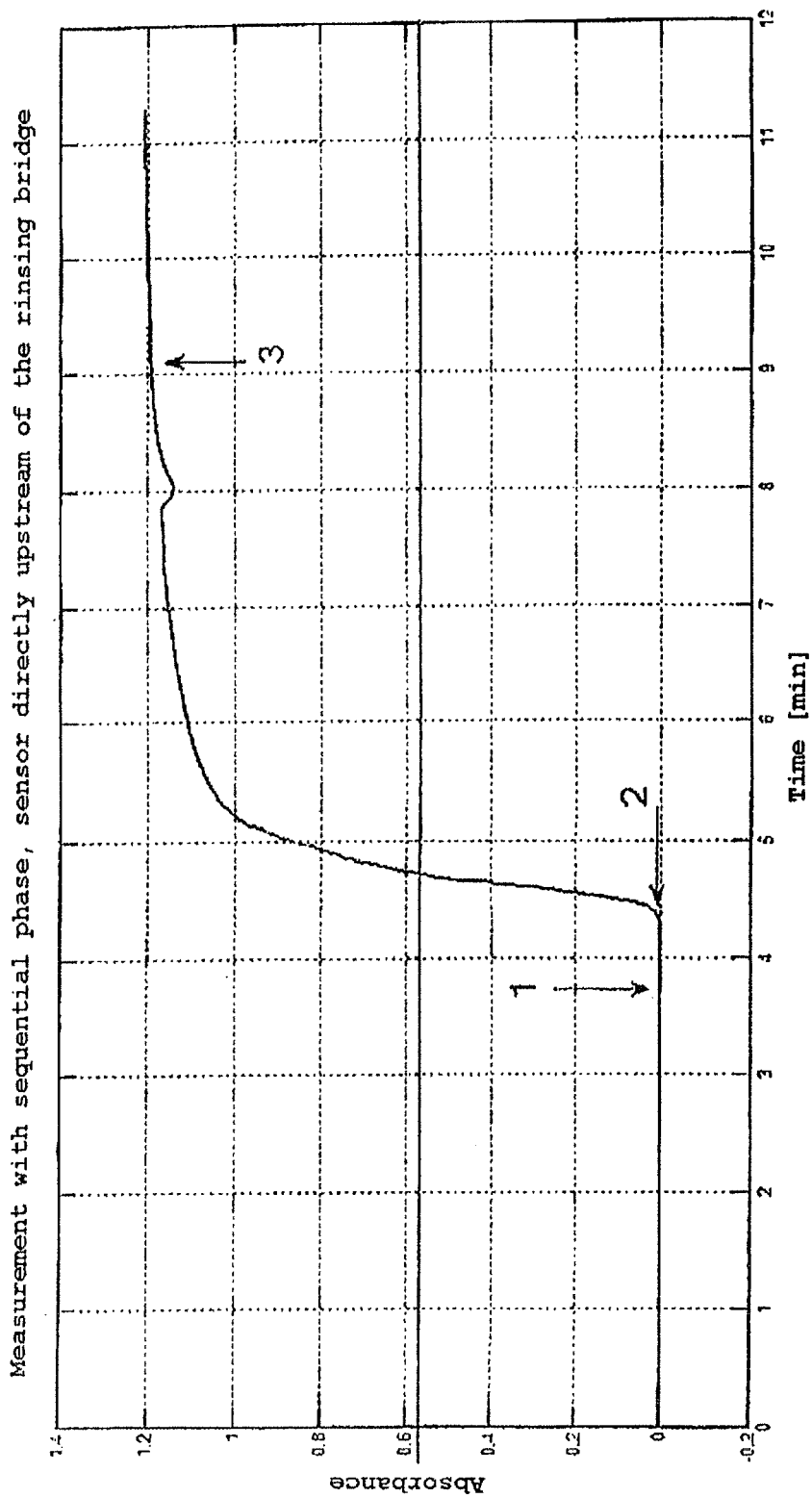
FIG. 9 shows the measuring result of a dialysis machine comprising a UV measuring device in a conventional position and FIG. 10 shows a comparison of the reaction delay to a concentration impulse of urea in a dialysis machine comprising a UV measuring device in a conventional position and in a proximal portion (close to the dialyzer) of the outflow of the dialysis liquid.

In the following, three examples will be set forth in which the difference between the prior art and the invention can be clearly seen. Here, reference is made to the measuring result according to FIG. 9.

In a first example from prior art, the concentration of urea in a conventional dialysis liquid is increased at time "1" at the dialyzer from zero to a constant value (83.4 mg/l) in a dialysis machine provided with a UV measuring device at a conventional position, by taking out the machine with running blood pump from the bypass at time "1". The flow of the dialysis liquid is constantly 500 ml/min, corresponding to a realistic flow speed of the dialysis liquid for a hemodialysis. The temperature of the dialysis liquid at the place of the UV measuring device is approximately 35° C. This also corresponds to the usual conditions of a hemodialysis. It occurs not until 30 to 40 seconds later that first urea molecules arrive at the sensor, i.e. at time "2". Since the addition of the urea, more than 5 minutes will have lapsed until the signal is entirely developed, i.e. to time "3". It can also be taken from FIG. 9 that the slow increase is due to the mixing effect which has been described above.

In a second example from the prior art, a concentration impulse which is clearly outlined in temporal regard, has a duration of 45 sec and is apparent in FIG. 5 as a rectangular impulse, is applied in a dialysis machine comprising a UV measuring device at a conventional position. This impulse is achieved by means of a saturation of a limited, clearly confined volume of a dialysis liquid in the dialyzer, which is pumped out subsequently. All further test conditions are the same as in the first example above. As a result of said concentration impulse, the absorption on the UV measuring device is measured for four different runs. Having passed the outflow-side dialysis liquid path in the dialysis machine, the signal loses its original shape and fades. The start and end points of the impulse cannot be clearly determined from the signal of the UV measuring device. The concentration profile has a strongly rounded appearance and there occurs a long sloping edge at the end of the impulse and a somewhat shorter edge at the start of the impulse, which is due for instance to diffusion effects or to effects attributable to the flow profile on the path through the machine fluidics, as has already been explained in the introductory part of the description. Due to the mixing effect, which depends on the fluid path between the dialyzer and the UV measuring device, the reproducibility of the measured values is negatively affected, too. This can be seen in FIG. 5 above all on the basis of the quality of the edges of the concentration impulse, but also by reference to the height of the absorption maximum. Four tests under identical requirements showed a dispersion of the results which was not negligible.

In a third example, the reaction delay to a concentration impulse of urea in a dialysis machine comprising a UV measuring device at a conventional position (in the central portion of the outflow of the dialysis liquid and downstream of the balancing equipment in flow direction) is compared with the one comprising a UV measuring device in the proximal portion of the outflow of the dialysis liquid. The course of the two curves is to be seen in FIG. 10. If the UV measuring device is provided in the position according to aspects of the invention, the concentration impulse can be detected at a significantly earlier point in time. Here too, the already known delay effect can be identified. The signal, which originally was a smooth one, shows steps downstream of the balancing equipment due to mixing effects, if the measurement is performed with high temporal resolution. Any non-laminar to turbulent flow conditions in and around the balancing equipment contribute here as well.

In summary, the invention relates to a device for extracorporeal blood treatment, comprising a detection equipment (14, 14a) for detecting uremic toxins in a used dialysis liquid preferably by measuring the absorbance, the detection equipment (14, 14a) being provided in such a position downstream the outflow (13) of the dialysis liquid from a filter element that at least one of the following requirements is fulfilled:

a) the filling volume of the fluid line and of the components starting from the outflow of the used dialysis liquid from the filter element to the detection equipment (14, 14a) is less than or equal to 100 ml, preferably less than or equal to 50 ml, preferably less than or equal to 35 ml, preferably less than or equal to 30 ml, preferably less than or equal to 15 ml, preferably less than or equal to 7 ml and b) the length of the fluid line starting from the outflow of the used dialysis liquid from the filter element to the detection equipment (14, 14a) is at most 250 cm, preferably less than or equal to 200 cm, preferably less than or equal to 150 cm, preferably less than or equal to 100 cm, preferably less than or equal to 50 cm, preferably less than or equal to 20 cm.

The invention claimed is:

1. A device for extracorporeal blood treatment of blood of a patient, comprising:
   a filter element which is subdivided into a blood-sided chamber and a dialysis liquid-side chamber and comprises an inflow for dialysis liquid to the dialysis liquid-side chamber and an outflow for the dialysis liquid from the dialysis liquid-side chamber,
   a fluid line coupled to the outflow for the dialysis liquid, wherein the fluid line is configured to conduct used dialysis liquid from the dialysis liquid-side chamber via the outflow,
   a bypass line selectively establishing a fluid connection between the inflow of the dialysis liquid-side chamber and the fluid line, the fluid connection bypassing the filter element, and a valve arranged on the fluid line downstream of the dialysis liquid-side chamber and upstream of the bypass line and further comprising
   a detection equipment arranged on the fluid line downstream from the outflow of the dialysis liquid from the dialysis liquid-side chamber and between the valve and the dialysis liquid-side chamber, wherein the detection equipment is adapted to measure a concentration and/or concentration change of at least one metabolic product from the blood of the patient in the used dialysis liquid, and wherein the detection equipment is further configured to output measurement values corresponding to the measured concentration and/or concentration change of the at least one metabolic product,
   wherein
   the fluid line has a fixed internal filling volume starting from the outflow from the filter element and ending with the detection equipment, and
   the detection equipment is arranged on the fluid line at a position downstream of the outflow of the dialysis liquid from the dialysis liquid-side chamber of the filter element, which position fulfills at least one of the following requirements:
   a) the fixed internal filling volume of the fluid line is less than or equal to 100 ml; or
   b) the length of the fluid line starting from the outflow from the filter element to the detection equipment is at most 250 cm;

such that diffusive degeneration of the concentration and/or the concentration change of the at least one metabolic product, and/or temporal delay of measurements by the detecting equipment, is avoided.

2. The device for extracorporeal blood treatment according to claim 1, further comprising a device housing, the detection equipment being provided within the device housing and the filter element being arranged outside the device housing, the filter element being fluidly connected to the detection equipment via a housing feedthrough.

3. The device according to claim 2, wherein the detection equipment is disposed on the housing feedthrough at an inner side or an outer side of a wall of the device housing comprising the housing feedthrough.

4. The device for extracorporeal blood treatment according to claim 2, further comprising a pressure sensor which is arranged upstream of the detection equipment in the vicinity of the housing feedthrough.

5. The device for extracorporeal blood treatment according to claim 1, wherein an additional detection equipment is arranged on the fluid line downstream of the bypass line, in order to allow for a calibration of the additional detection equipment with fresh dialysis liquid when there is a bypass around the filter element.

6. The device for extracorporeal blood treatment according to claim 1, wherein an inner cross-section of the fluid line between the filter element and the detection equipment is between 3 mm and 7 mm.

7. The device for extracorporeal blood treatment according to claim 6, wherein the inner cross-section of the fluid line between the filter element and the detection equipment is substantially constant.

8. The device for extracorporeal blood treatment according to claim 6, wherein the inner cross-section of the fluid line between the filter element and the detection equipment is 5 mm.

9. The device for extracorporeal blood treatment according to claim 1, wherein the detection equipment comprises an optical sensor system in the form of a UV measuring device.

10. The device of claim 1, wherein the fixed internal filling volume is less than or equal to 30 ml.

11. The device of claim 1, wherein the length of the fluid line is less than or equal to 100 cm.

12. The device for extracorporeal blood treatment according to claim 1, further comprising fluidic components arranged on the fluid line starting from the outflow from the filter element and ending with the detection equipment, wherein the fixed internal filling volume of the fluid line including the arranged fluidic components is less than or equal to 100 ml.

* * * * *